United States Patent
Baykut et al.

(10) Patent No.: US 8,366,411 B2
(45) Date of Patent: Feb. 5, 2013

(54) AXIAL FLOW PUMP WITH A SPIRAL-SHAPED VANE

(76) Inventors: Doan Baykut, Binningen (CH); Goekhan Baykut, Bremen (DE); Felix Hirt, Winterthur (CH)

( * ) Notice: Subject to any disclaimer, the term of this patent is extended or adjusted under 35 U.S.C. 154(b) by 995 days.

(21) Appl. No.: 11/994,480

(22) PCT Filed: Jun. 30, 2006

(86) PCT No.: PCT/EP2006/006344
§ 371 (c)(1),
(2), (4) Date: Jul. 7, 2008

(87) PCT Pub. No.: WO2007/003351
PCT Pub. Date: Jan. 11, 2007

(65) Prior Publication Data
US 2008/0292478 A1    Nov. 27, 2008

(30) Foreign Application Priority Data
Jul. 1, 2005    (EP) .................................... 05405423

(51) Int. Cl.
*F04B 35/04*    (2006.01)
*F04B 35/00*    (2006.01)

(52) U.S. Cl. ...................... 417/356; 417/423.14; 600/16

(58) Field of Classification Search .................. 417/355, 417/356, 423.7, 423.14, 423.1; 600/16
See application file for complete search history.

(56) References Cited

U.S. PATENT DOCUMENTS

| | | | | |
|---|---|---|---|---|
| 1,534,451 | A * | 4/1925 | Kauter | 417/356 |
| 3,719,436 | A * | 3/1973 | McFarlin | 417/356 |
| 5,324,177 | A | 6/1994 | Golding et al. | |
| 5,368,457 | A * | 11/1994 | Watanabe et al. | 418/220 |
| 6,015,272 | A | 1/2000 | Antaki et al. | |
| 6,053,705 | A | 4/2000 | Schoeb et al. | |
| 6,109,887 | A | 8/2000 | Takura et al. | |
| 6,135,729 | A | 10/2000 | Aber et al. | |
| 6,290,640 | B1 * | 9/2001 | Goldowsky | 600/16 |
| 6,357,998 | B1 * | 3/2002 | Rosefsky | 415/66 |
| 6,527,520 | B2 | 3/2003 | Rosefsky | |

(Continued)

FOREIGN PATENT DOCUMENTS

| | | |
|---|---|---|
| GB | 2301399 | 12/1996 |
| JP | 2-149619 U1 | 12/1990 |

(Continued)

OTHER PUBLICATIONS

Japanese Patent Office of Oct. 4, 2011, Office Action of Japanese patent application No. 2008-518731 and corresponding search report.

*Primary Examiner* — Peter J Bertheaud
(74) *Attorney, Agent, or Firm* — Lowe Hauptman Ham & Berner LLP (57) ABSTRACT

An axial flow pump (10) is presented which includes a housing (1) with an inlet (2) and outlet (3) and a magnetically active rotor (5) in the housing which is provided with a passage (6) in the interior and with at least one spiral-shaped vane (7) in the passage, wherein the pitch of the vane (7) varies in the axial direction. The axial flow pump (10) furthermore includes an electromagnetic drive (4, 8) with a stator (8) which is arranged at the housing and cooperates with a magnetically active rotor.

11 Claims, 13 Drawing Sheets

U.S. PATENT DOCUMENTS

| | | |
|---|---|---|
| 6,527,521 B2 * | 3/2003 | Noda .......................... 417/355 |
| 6,592,335 B2 | 7/2003 | Rosefsky |
| 7,021,905 B2 * | 4/2006 | Torrey et al. ................. 417/356 |
| 7,118,356 B2 | 10/2006 | Ma et al. |
| 7,374,574 B2 | 5/2008 | Nuesser et al. |
| 7,467,929 B2 * | 12/2008 | Nusser et al. ................ 417/351 |
| 7,699,586 B2 * | 4/2010 | LaRose et al. ............... 417/356 |
| 2001/0009645 A1 | 7/2001 | Noda |
| 2002/0150465 A1 | 10/2002 | Rosefsky |
| 2004/0115038 A1 * | 6/2004 | Nuesser et al. ............... 415/75 |
| 2004/0241019 A1 * | 12/2004 | Goldowsky ................ 417/423.1 |

FOREIGN PATENT DOCUMENTS

| | | |
|---|---|---|
| JP | 2000054978 | 2/2000 |
| WO | 9618358 A1 | 6/1996 |
| WO | 01/02724 A1 | 1/2001 |
| WO | 2005002646 A1 | 1/2005 |

* cited by examiner

AXIAL FLOW PUMP WITH A SPIRAL-SHAPED VANE

CROSS REFERENCE TO RELATED APPLICATIONS

This is the U.S. national stage of International application PCT/EP2006/006344, filed Jun. 30, 2006 designating the United States which claims the benefit of European application 05405423.4, filed Jul. 1, 2005.

BACKGROUND OF THE INVENTION

The invention relates to an axial flow pump.

Pumps for applications with small pressure differentials of typically 100 hPA to 150 hPa and comparatively large volume flows, such as blood pumps, for example, are advantageously designed as axial flow pumps. Document WO 96/18358 describes a blood pump of this type having a pipe-shaped pump housing in which a rotor is in each case rotatably supported in a bearing at the ends. The described rotor includes a cylindrical rotor body, with a hub adjacent to it on the inlet side and an end piece adjacent to it on the outlet side, each of which run out into a bearing spigot. Furthermore, a plurality of curved vanes are provided on the rotor body and a permanent magnet is provided in the interior of the rotor body to magnetically drive the rotor. The comparatively large contact area of the hub, rotor body and end piece with the blood and the bearings arranged in the volume flow promote the creation of deposits and thromboses.

Patent specification U.S. Pat. No. 6,527,521 B2 discloses a further development of a blood pump having a pipe-shaped pump housing in which a hollow cylindrical rotor is arranged which is provided with permanent magnets at the periphery. The rotor is chamfered at both ends and the pump housing is tapered at the corresponding points such that the gap between the rotor and the pump housing is kept small. A stator to drive the rotor magnetically and a plurality of permanent magnets to support the rotor magnetically are arranged on the outer surface of the pump housing. A spiral-shaped vane with a constant pitch is formed on the inner surface of the rotor such that the centre of the rotor is kept open.

SUMMARY OF THE INVENTION

The axial flow blood pumps of the prior art have the disadvantage that either the contact area with the main volume flow of the blood is comparatively large due to the closed rotor body and the hub or, in the case of a hollow cylindrical rotor, the achievable pressure is very small due to the constant pitch of the vane and the open rotor centre. In addition, the discharge angle is unfavourable in the latter design. A further disadvantage of the axial flow blood pumps of the prior art relates to the support of the rotor. In the blood pump described in WO 96/18358, the spigot bearings are located in the main volume flow, which has proved to be unfavourable. In the blood pump disclosed in U.S. Pat. No. 6,527,521 B2, the rotor is admittedly supported in a contact-free manner, i.e. magnetically, but exclusively passively, which is not classified as optimal, in particular when inertial forces act on the rotor and/or the pressure varies.

It is the object of the invention to provide a pump driven in a contact-free manner for small pressure differentials of typically 100 hPa, 150 hPa or 200 hPa which is in particular suitable as a blood pump, for example as a ventricle assist device, and which has a comparatively small contact area with the main volume flow.

The axial flow pump in accordance with the invention includes a housing with an inlet and an outlet and a rotor in the housing, for example an elongate-shaped rotor which is provided with a passage in the interior and with at least one spiral-shaped transport element, for example a spiral-shaped vane, in the passage, with the pitch of the transport element varying in the axial direction. The axial flow pump furthermore includes an electromagnetic drive to drive the rotor, with a stator being provided at the housing and the rotor or a part thereof being made magnetically active.

In a preferred embodiment variant, the pitch of the transport element increases in the direction of the outlet and in a further preferred embodiment variant, the centre of the rotor is open over at least a part of the rotor length. The centre of the rotor toward the inlet is preferably open and/or preferably closed toward the outlet.

In a further preferred embodiment variant, the axial flow pump includes an additional pump stage whose centre is closed toward the outlet, in particular a second pump stage which is made axially or semi-axially and/or is provided with a hub at the centre.

The transport element and/or an edge thereof preferably has a rounded or pointed profile. The transport element preferably includes one or more vanes and/or holes and/or slits and/or local elevated portions and/or local recesses.

In a further preferred embodiment variant, a gap of at least 0.3 mm width, in particular at least 0.6 mm width, is provided between the housing and the rotor in operation. At least one external transport element is preferably provided at the outer surface of the rotor and includes, for example, one or more vanes and/or holes and/or slits and/or local elevated portions and/or local recesses.

In a further preferred embodiment variant, at least one part of the rotor contains a permanently magnetic or soft magnetic material or the rotor includes at least one short-circuit turn. The electromagnetic drive is preferably simultaneously made as a magnetic bearing. At least two magnetic bearings, which are arranged axially offset, are preferably provided in the axial flow pump, with at least one of the magnetic bearings being arranged, for example, in the inlet side end region of the rotor and/or in the outlet side end region of the rotor.

In a further preferred embodiment variant, the axial flow pump includes at least one guide element which is arranged in the inlet region or between the housing and the rotor or in the outlet region at the housing. The axial flow pump preferably includes at least two respective guide elements arranged in the inlet region and/or in the outlet region at the housing.

In a further preferred embodiment variant, the axial flow pump includes one or two ring-shaped rotor caps which are, for example, fastened to holding elements, preferably holding vanes, and which are arranged before and/or after the rotor in the direction of flow.

In a further preferred embodiment variant, at least one coupling part is provided at the housing for the connection of the axial flow pump to an inlet cannula and/or outlet cannula.

The axial flow pump in accordance with the invention has the advantage that pressure differentials of, for example, 100 hPa, 150 hPa or 200 hPa can be achieved and that it can be used as an implantable blood pump. It is also advantageous that the axial flow pump in accordance with the invention has a comparatively small contact area with the main volume flow and that the blood cells do not meet the resistance of a hub. Furthermore, a better washing around is possible due to the comparatively wide gap between the housing and the rotor.

Further advantageous embodiments can be seen from the dependent claims and from the drawing.

BRIEF DESCRIPTION OF THE FIGURES

The invention will be explained in more detail in the following with reference to the embodiments and to the drawing. There are shown.

DESCRIPTION OF VARIOUS AND PREFERRED EMBODIMENTS OF THE INVENTION

Figure 1:
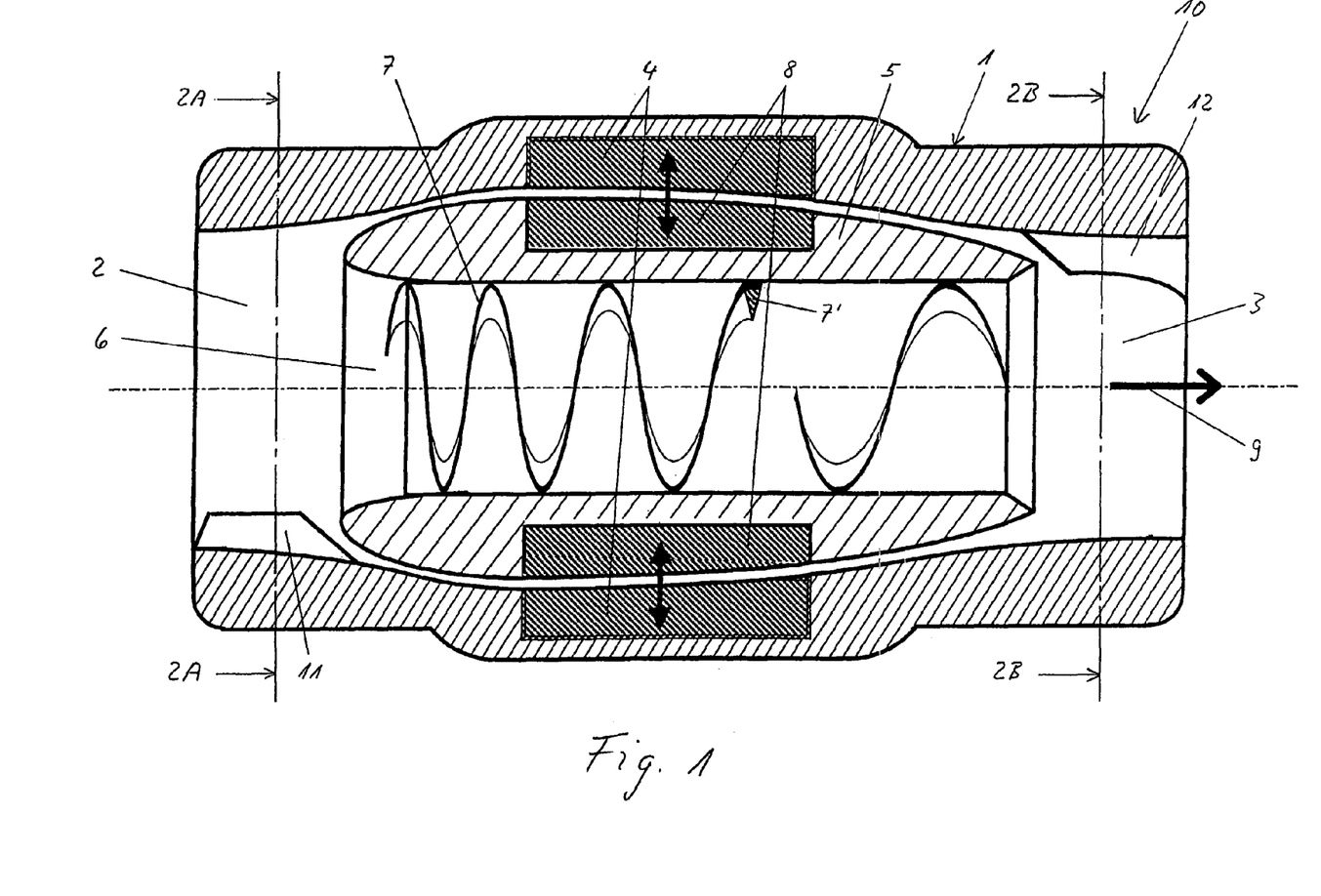
FIG. 1 a longitudinal section of an embodiment of an axial flow pump in accordance with the present invention.

FIG. 1 shows a longitudinal section through an embodiment of an axial pump in accordance with the present invention. In the embodiment shown, the axial flow pump 10 includes a housing 1 with an inlet 2 and an outlet 3 and a rotatably arranged rotor 5, for example an elongate-shaped rotor, in the housing. The housing 1 is advantageously made, as shown in FIG. 1, as an elongate hollow body with a circular opening in the interior which can, for example, have a changed diameter, e.g. an enlarged diameter, in the region of the rotor. Arrow 9 designates the throughflow direction of the axial flow pump.

The rotor 5 is provided with a passage 6 in the interior and can e.g. be made as a hollow cylinder or, as shown in FIG. 1, have a shape adapted to the flow. A spiral-shaped transport element 7 is arranged on the inner surface of the rotor in the passage 6 and is made, for example, as a spiral-shaped vane, with the pitch of the transport element varying in the axial direction. If required, a plurality of transport elements can also be provided in the passage 6.

The axial flow pump of the embodiment shown in FIG. 1 furthermore includes an electromagnetic drive, preferably to drive the rotor 5 magnetically, i.e. in a contact-free manner, with a stator 4 being provided at the housing 1 and the rotor or a part 8 thereof being made magnetically active, for example, in that the rotor or a part thereof includes a permanently magnetic material or a soft magnetic material or at least one short-circuit turn. The stator 4, for example, includes a plurality of windings which are arranged on a soft magnetic core to generate a rotary field in operation. The electromagnetic drive is simultaneously made as a magnetic bearing in an advantageous embodiment.

The axial flow pump in accordance with the present invention is, for example, suitable as a blood pump, in particular as an implantable blood pump. The surfaces coming into contact with blood are advantageously partly or fully provided with a blood-compatible coating, e.g. with a coating containing diamond-like carbon (DLC).

Figure 13:
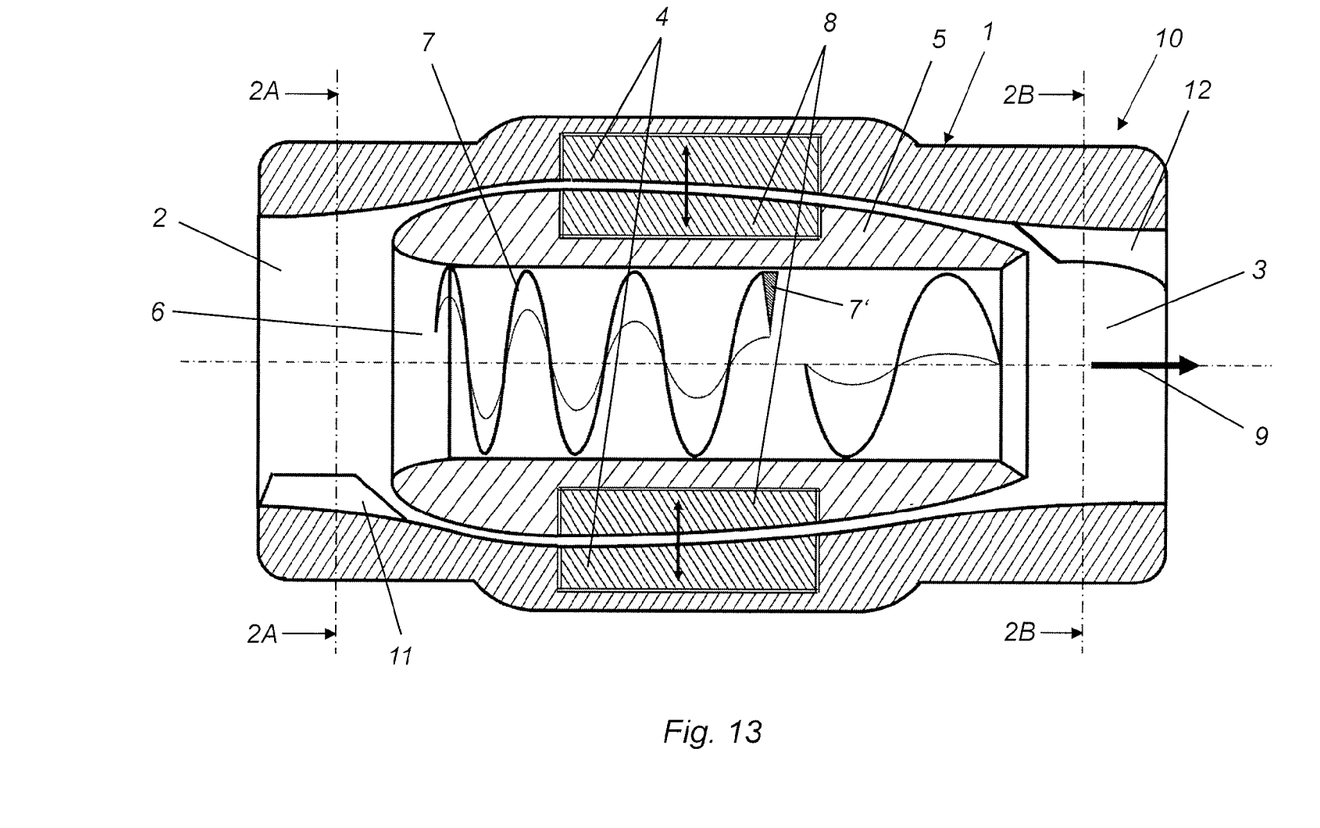
FIG. 13 a longitudinal section of an axial flow pump in accordance with an embodiment of the present invention.

In an advantageous embodiment variant, the pitch, or optionally the pitch angle or the pitch height of the transport element 7 increases in the direction of the outlet 3, whereby the outlet pressure and/or the discharge angle can, for example, be increased. In a further advantageous embodiment variant (as seen, for example, in FIG. 13), the centre of the rotor is open over at least a part of the rotor length, with the cross-section left open within the transport element 7 being able to vary over the length of the rotor, for example, in that the cross-section left open reduces towards the outlet so that the cross-section left open is comparatively small at the end of the rotor at the outlet side or the transport element 7 extends into the centre of the rotor at the end at the outlet side. In an advantageous embodiment, the centre of the rotor is open towards the inlet and/or closed towards the outlet.

The transport element 7 and/or an edge thereof advantageously has a rounded or pointed profile 7', for example a triangular profile, which is tapered towards the rotor axis, or a profile rounded towards the rotor axis or, optionally, rounded and/or chamfered inlet and outlet edges. In a further advantageous embodiment, the transport element optionally includes holes, slits, local elevated regions and/or local recesses.

Figure 2A:
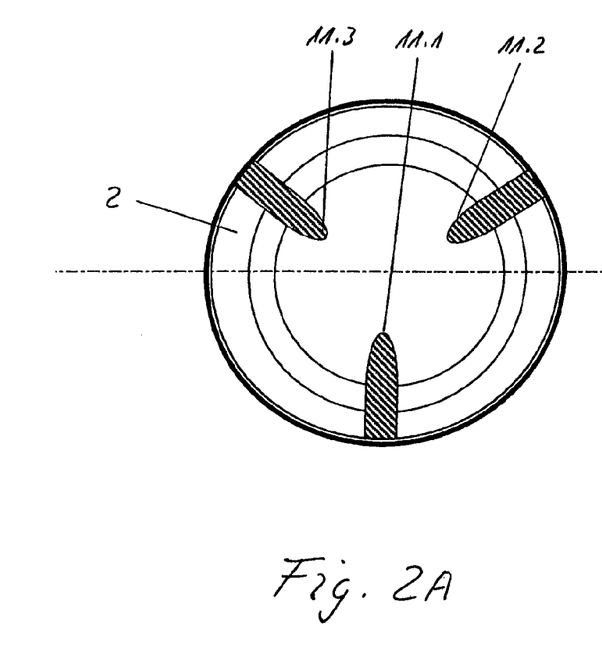
FIGS. 2A, B cross-sections through the inlet region and the outlet region of the axial flow pump in accordance with the embodiment shown in FIG. 1.
Figure 2B:
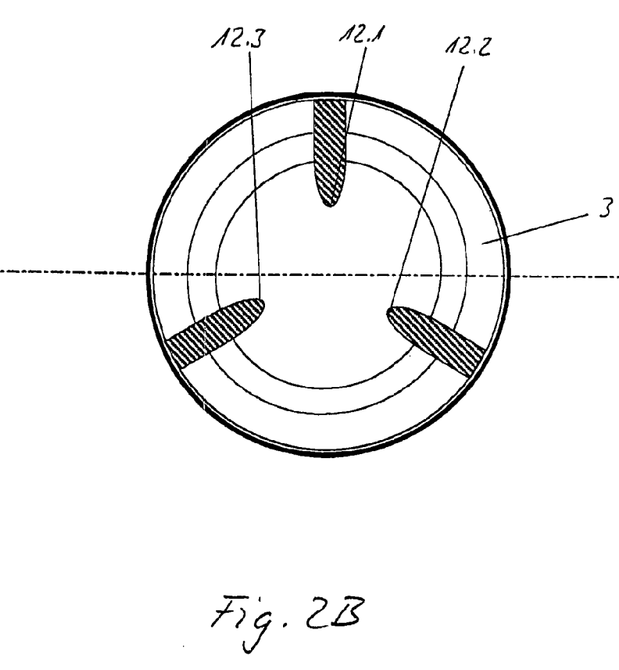

FIGS. 2A and 2B show cross-sections through the inlet region and the outlet region of the axial flow pump in accordance with the embodiment shown in FIG. 1. In this embodiment, three respective axial guide vanes 11.1-11.3, 12.1-12.3 are arranged in the inlet region and in the outlet region respectively of the axial flow pump. It is naturally also possible to arrange guide elements either only in the inlet region or only in the outlet region. The number of the guide elements is likewise selectable. Typically, arrangements of two to four guide vanes are provided. Furthermore, the shape and the profile of the guide elements can also be matched to the particular conditions, for example in that axial, obliquely running or curved guide vanes are provided or guide vanes or guide vane edges with a rounded, running out or tapered profile.

Figure 3:
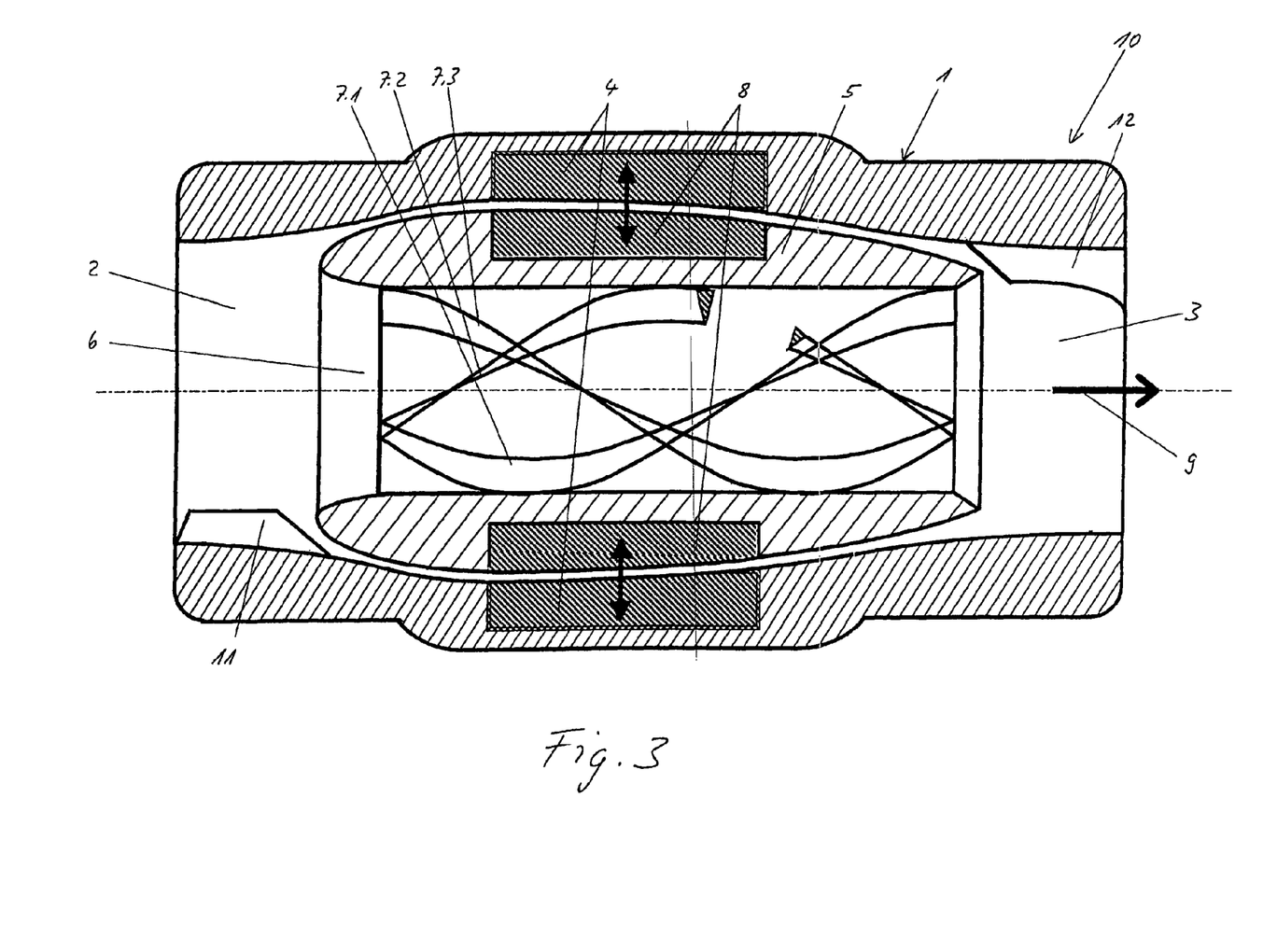
FIG. 3 an embodiment variant with a plurality of transport elements in the interior of the rotor.

In the embodiment variant shown in FIG. 3, the rotor 5 is provided with a plurality of transport elements 7.1-7.3 on the interior. In this case, it can be advantageous to increase the pitch of the transport elements with respect to the embodiment with only one transport element.

Figure 4:
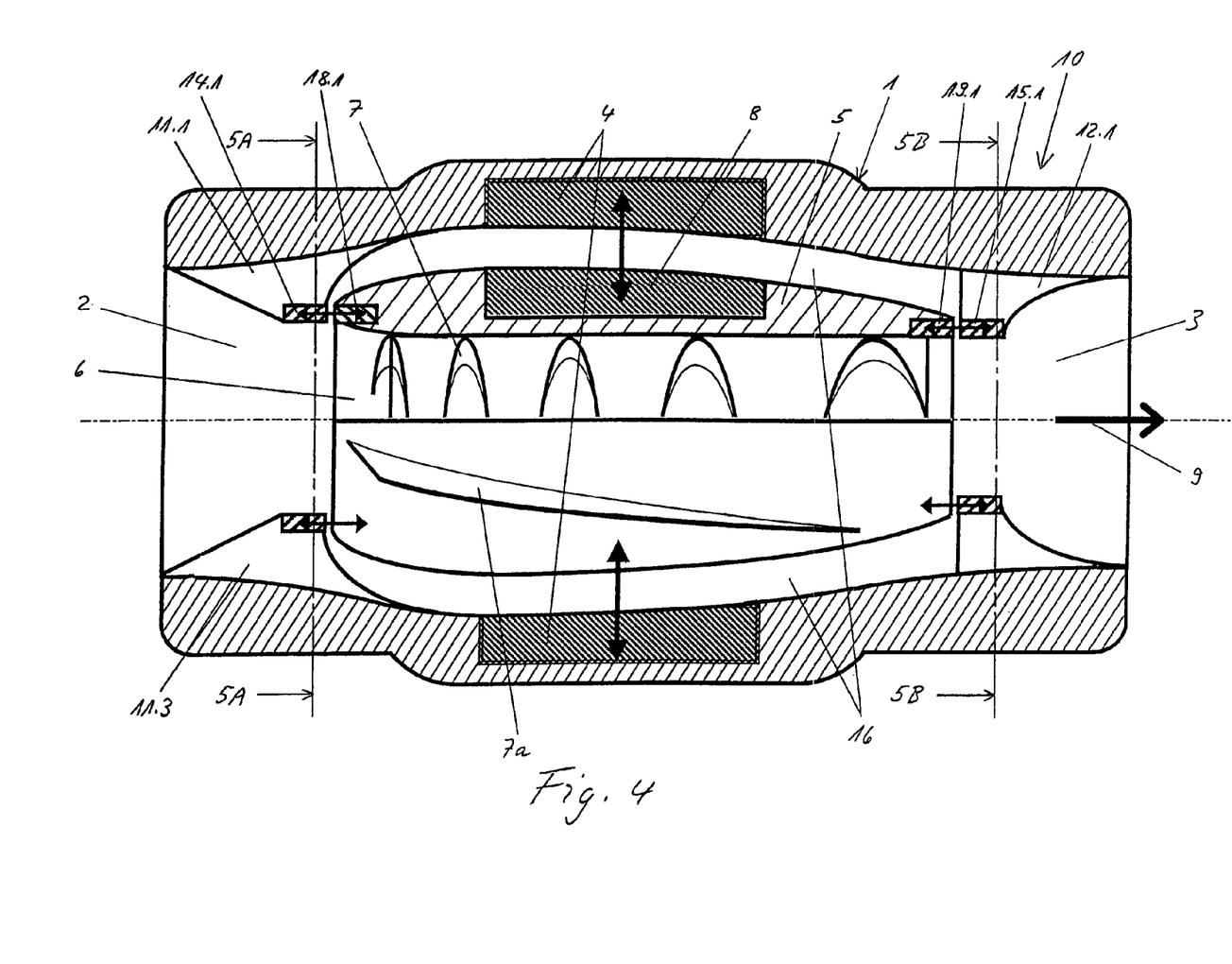
FIG. 4 a further embodiment variant with a comparatively wide gap between the housing and the rotor.

FIG. 4 shows a further embodiment variant with a comparatively wide gap 16 between the housing 1 and the rotor 5 in operation, for example with a gap of at least 0.3 mm width, in particular at least 0.6 mm or 1 mm width. In an advantageous embodiment, at least one external transport element 7a, for example in the form of vanes and/or holes and/or slits and/or local elevated portions and/or local recesses, is provided at the outer surface of the rotor 5.

In an advantageous embodiment variant, one or more magnetic bearings can be provided in the axial flow pump to support the rotor 5 in a contact-free manner, for example in that the electromagnetic drive 4, 8 is simultaneously made as a magnetic bearing and/or in that the axial flow pump is provided with one or more magnetic bearings arranged axially offset. In the embodiment variant shown in FIG. 4, magnetic bearings {14.1, 18.1}, {15.1, 19.1}, which can, for example, be made as passive magnetic bearings, are respectively provided in the end region of the rotor 5 at the inlet side and/or at the outlet side. The guide vanes 11.1-11.4 and 12.1-12.4 are provided for this purpose with permanent magnets 14.1 and 15.1 in the part adjoining the rotor, whereas the rotor is fitted with one or more respective permanent magnets 18.1, 19.1 in the end region at the inlet side and at the outlet side. Instead of a plurality of permanent magnets in each rotor end region, a respective ring-shaped permanent magnetic can also be used in each rotor end region. As required, the guide vanes 11.1-11.4 and 12.1-12.4 can also be provided with electromagnets 14.1 and 15.1 with which the position of the rotor 5 can be actively stabilised.

Figure 5A:
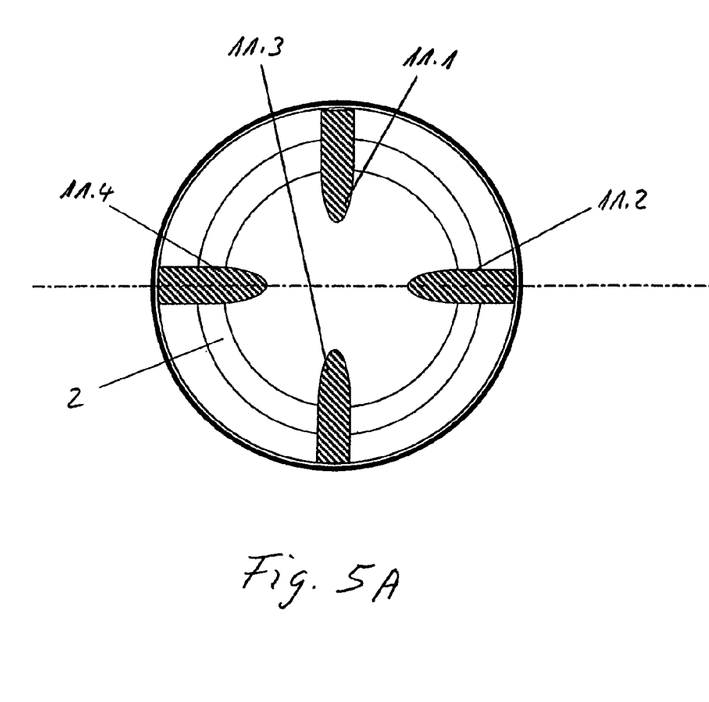
FIGS. 5A, B cross-sections through the inlet region and the outlet region of the axial flow pump in accordance with the embodiment variant shown in FIG. 4.
Figure 5B:
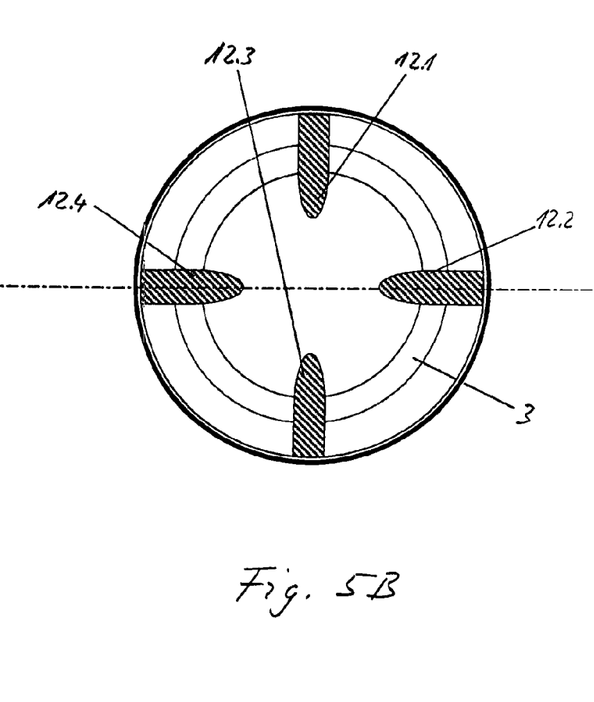

FIGS. 5A and 5B show cross-sections through the inlet region and the outlet region of the axial flow pump in accordance with the embodiment variant shown in FIG. 4. In this embodiment variant, four respective guide vanes 11.1-11.4, 12.1-12.4 are arranged in the inlet region and outlet region of the axial flow pump respectively.

Figure 6:
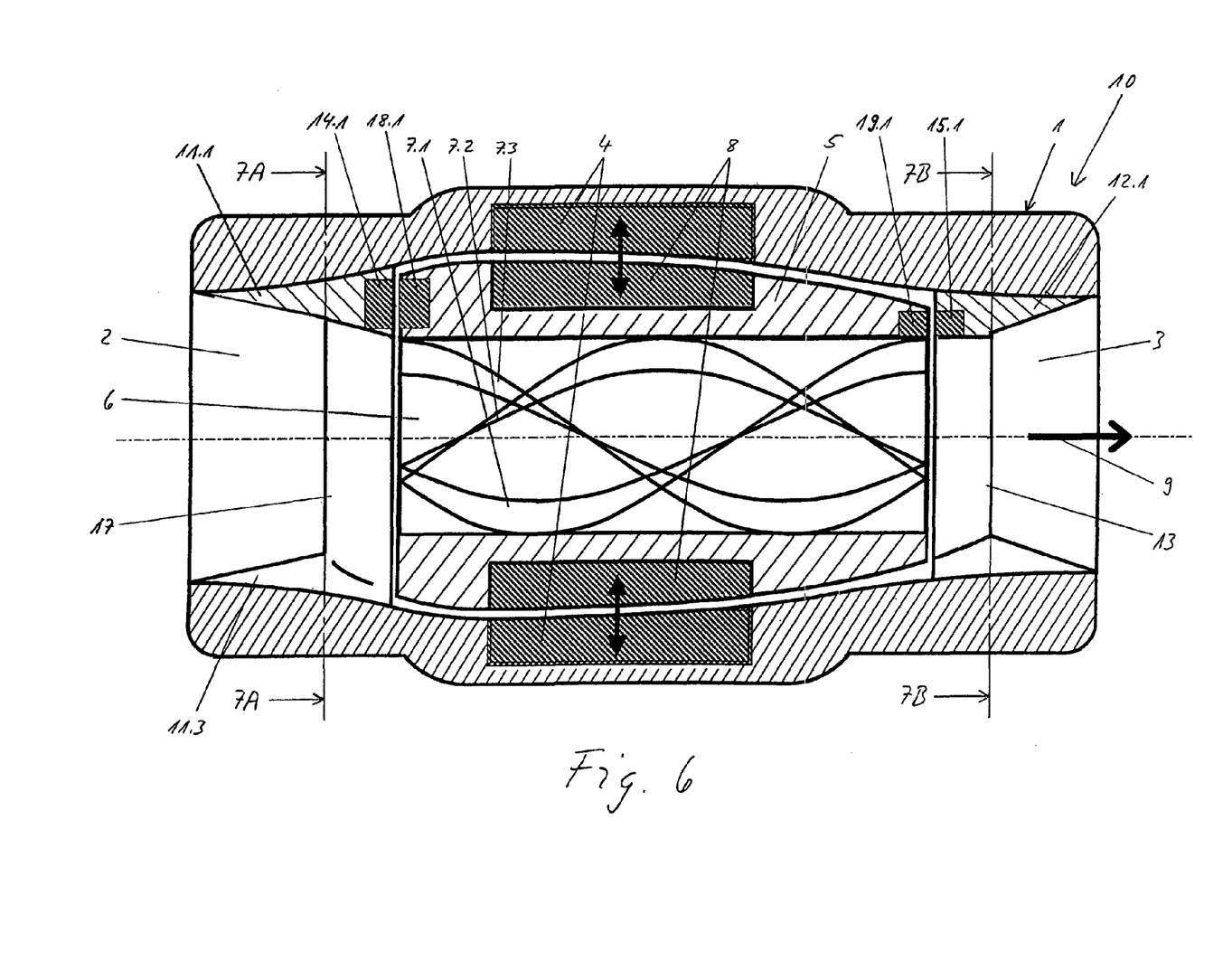
FIG. 6 a longitudinal section of a second embodiment of an axial flow pump in accordance with the present invention.

FIG. 6 shows a longitudinal section through a second embodiment of an axial flow pump in accordance with the present invention. The second embodiment differs from the first embodiment in accordance with FIG. 1 in particular in that rotor caps 17, 13, which are advantageously ring-shaped, are arranged before and/or after the rotor 5 in the direction of flow. The other features of the second embodiment are already known from the description of the first embodiment, with the exception of the number of transport elements in the interior of the rotor which was described in connection with the embodiment variant shown in FIG. 3, and with the exception of the magnetic bearings at the end of the rotor on the inlet side and on the outlet side, which were explained in connection with the embodiment variant shown in FIG. 4.

The rotor caps 13, 17 have the advantage that larger permanent magnets 14.1 and 15.1 can be arranged therein, for example a ring-shaped permanent magnet 14.1 in the rotor cap 17 at the inlet side which can absorb larger axial forces. Since the axial force resulting due to the pressure differential between the inlet and the outlet has to be completely absorbed by the magnetic bearings with a contact-free support of the rotor, a greater pressure differential can be generated using the axial flow pump in accordance with the second embodiment. If required, instead of the permanent magnets, electromagnets can also be provided in the rotor caps with which the position of the rotor can be actively stabilised.

Figure 7A:
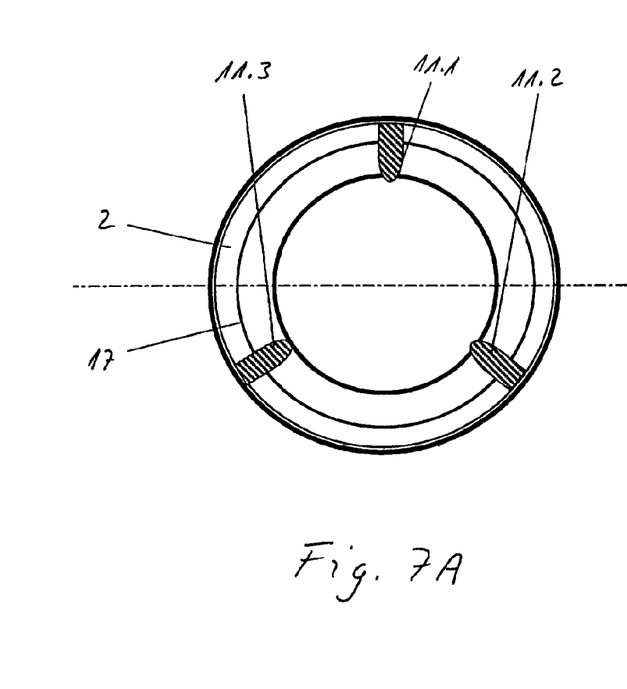
FIGS. 7A, B cross-sections through the inlet region and the outlet region of the axial flow pump in accordance with the embodiment shown in FIG. 6.
Figure 7B:
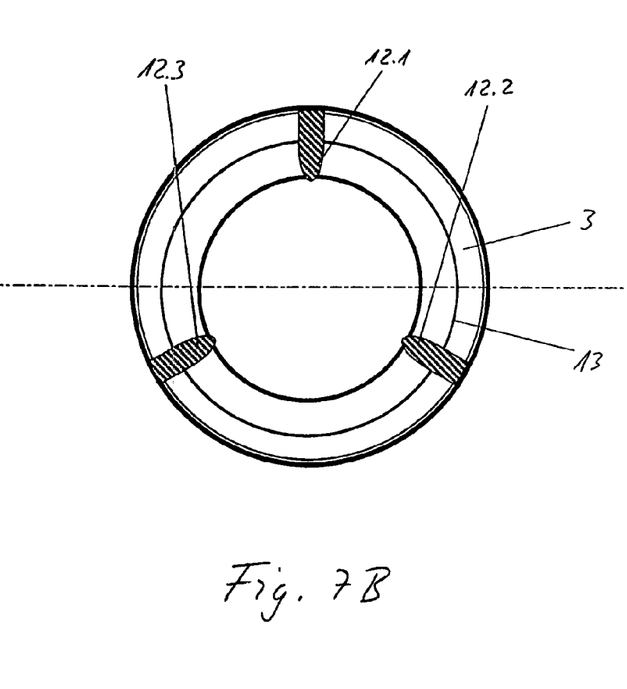

FIGS. 7A and 7B show cross-sections through the inlet region and the outlet region of the axial flow pump in accordance with the embodiment shown in FIG. 6. In this embodiment, three respective guide vanes 11.1-11.3, 12.1-12.3 are arranged in the inlet region and in the outlet region respectively of the axial flow pump and can simultaneously be made e.g. as holding vanes for the rotor caps 13, 17.

Figure 8:
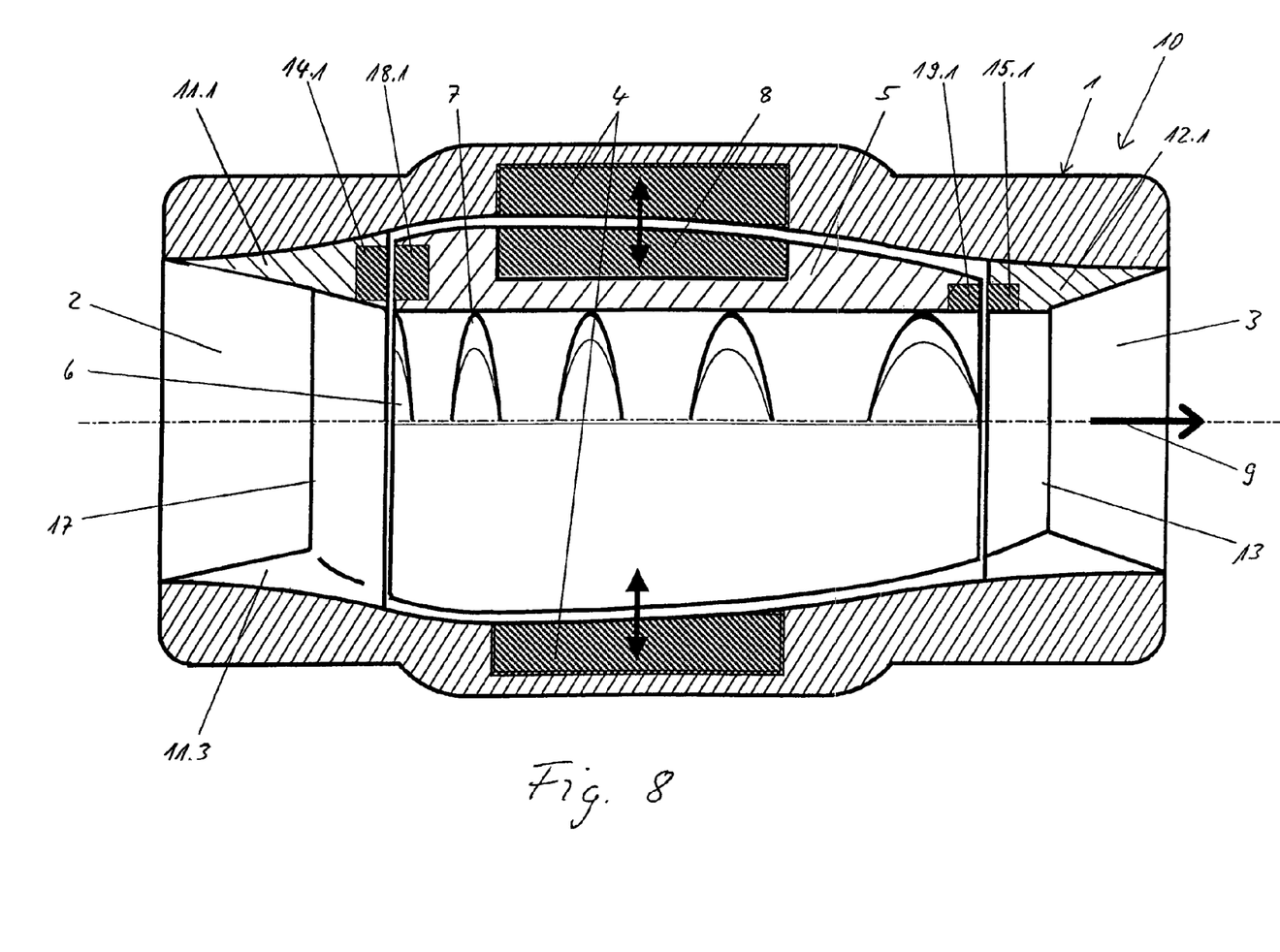
FIG. 8 an embodiment variant with respect to the embodiment shown in FIG. 6 with only one transport element in the interior of the rotor.

In the embodiment variant shown in FIG. 8, the rotor 5 is provided with a single transport element 7 on the interior. The other features correspond to those of the second embodiment in accordance with FIG. 6.

Figure 9:
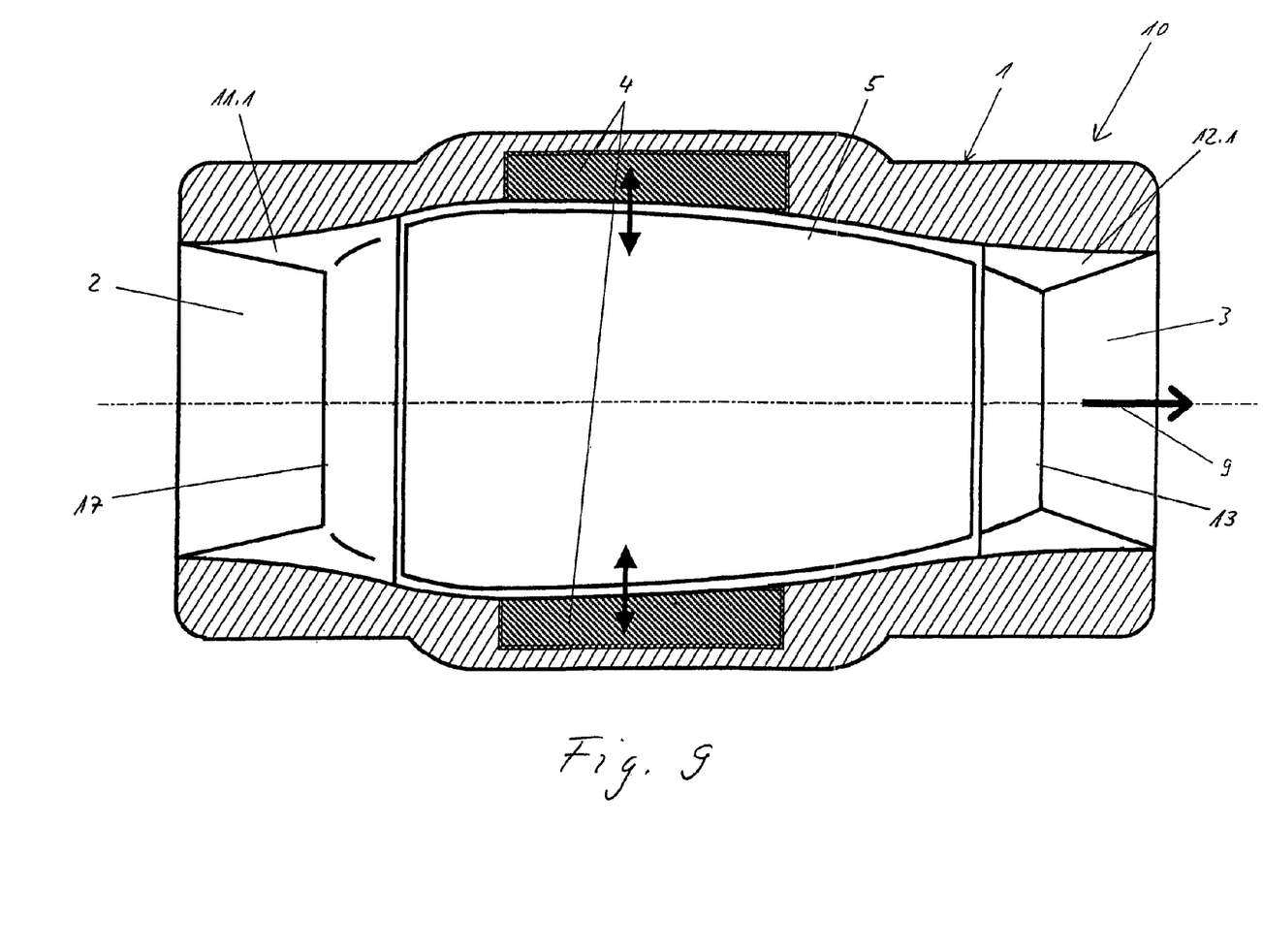
FIG. 9 a longitudinal section through the housing of the embodiment shown in FIG. 6.

FIG. 9 shows a further view of the second embodiment in accordance with FIG. 6. In this view, the housing is shown in the longitudinal section, whereas the rotor 5, the rotor caps 13, 17 and the guide vanes 11.1, 12.1 are reproduced in the plan view.

Figure 10:
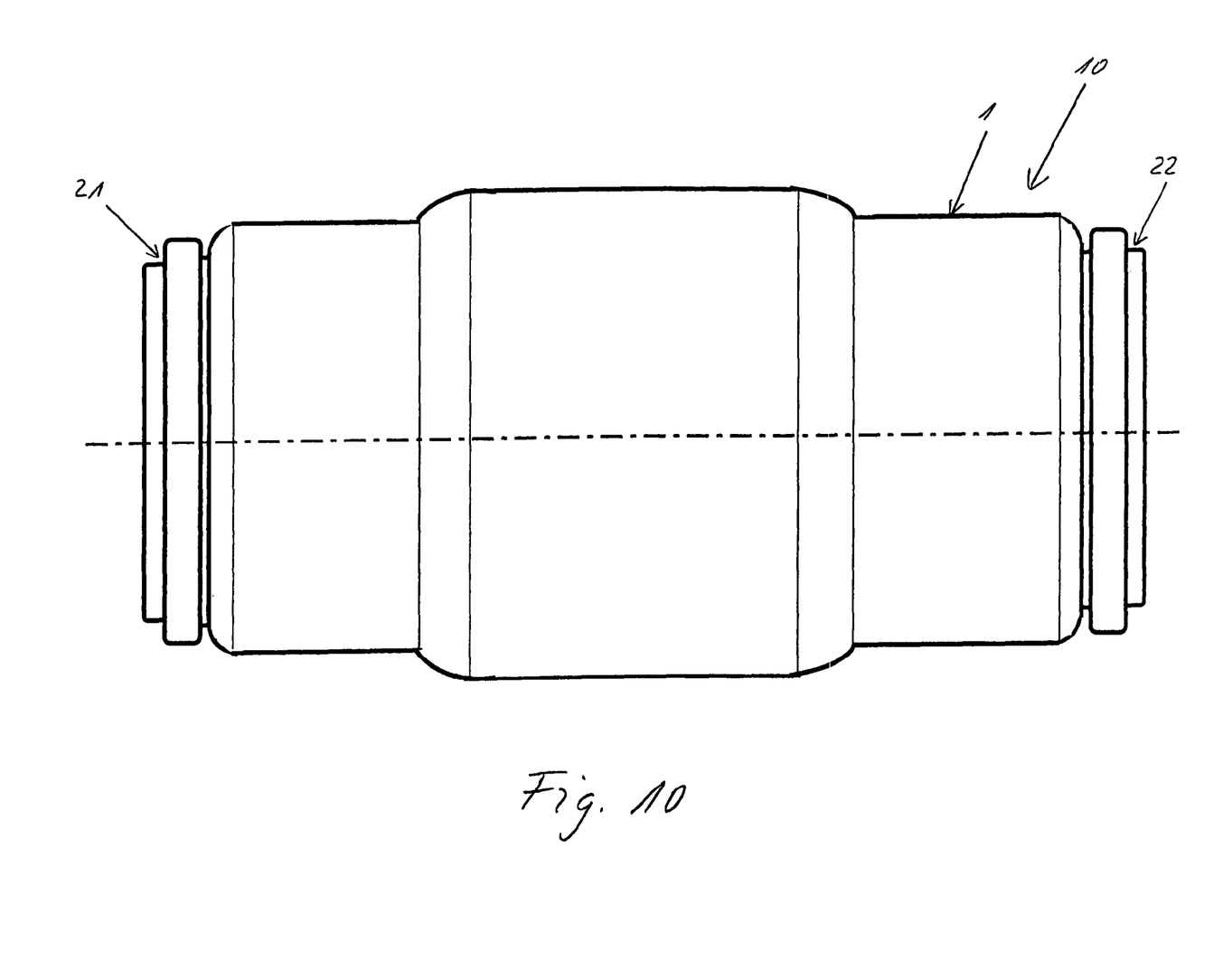
FIG. 10 an external view of an embodiment variant with coupling parts.

FIG. 10 shows a further preferred embodiment variant. In this embodiment variant, the axial flow pump 10 includes a housing 1 and one respective coupling part 21, 22 at the inlet side and at the outlet side respectively, with an inlet cannula or an outlet cannula respectively being able to be connected to said coupling part.

Figure 11:
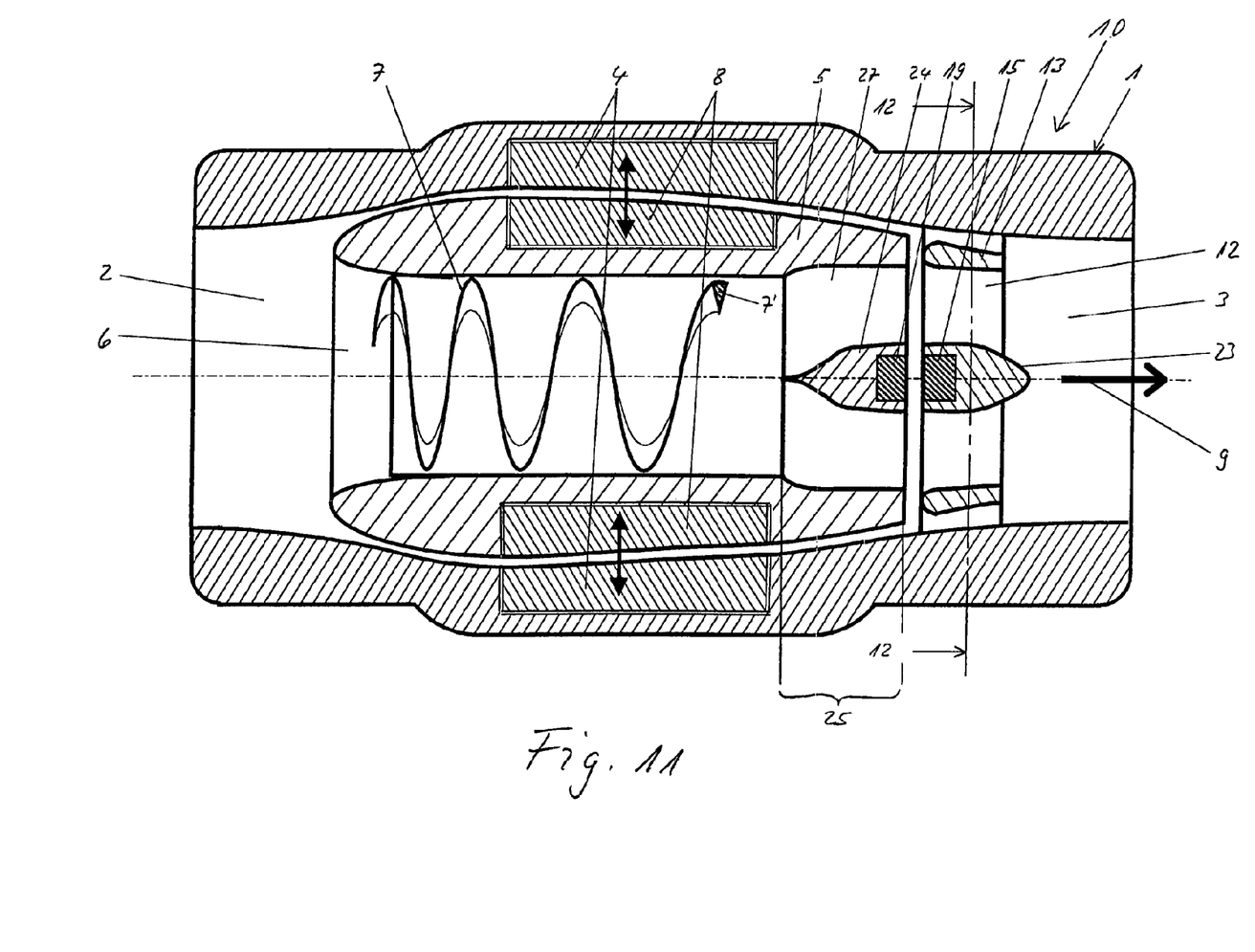
FIG. 11 a longitudinal section of a further embodiment of an axial flow pump in accordance with the present invention.

FIG. 11 shows a longitudinal section through a further embodiment of an axial flow pump in accordance with the present invention. The embodiment shown differs from the first embodiment in accordance with FIG. 1 in particular in that the pump 10 includes an additional pump stage 25 whose centre is closed towards the outlet 3. The additional pump stage 25 can be formed in the rotor 5, for example, as shown in FIG. 11. It is, however, also possible to provide a separate rotor for the additional pump stage which can be fitted with its own drive if necessary. As shown in FIG. 11, the additional pump stage can include a hub 24 and one or more transport elements 27 which can e.g. be made as vanes. The additional pump stage can be made axially or semi-axially. A pump of this type with an additional pump stage represents a separate and independent invention which can be protected in its own patent application.

In a preferred embodiment variant, the pump with an additional pump stage includes at least one guide element on the outlet side, for example a guide ring 13 with holding elements 12 which can be made as guide vanes. If required, a cap 23 can be provided in the centre at the holding elements or guide vanes.

In a further preferred embodiment variant, a magnetic bearing 19, 15 and/or an electromagnetic drive apparatus is/are provided in the hub 24 and in the cap 23.

Figure 12:
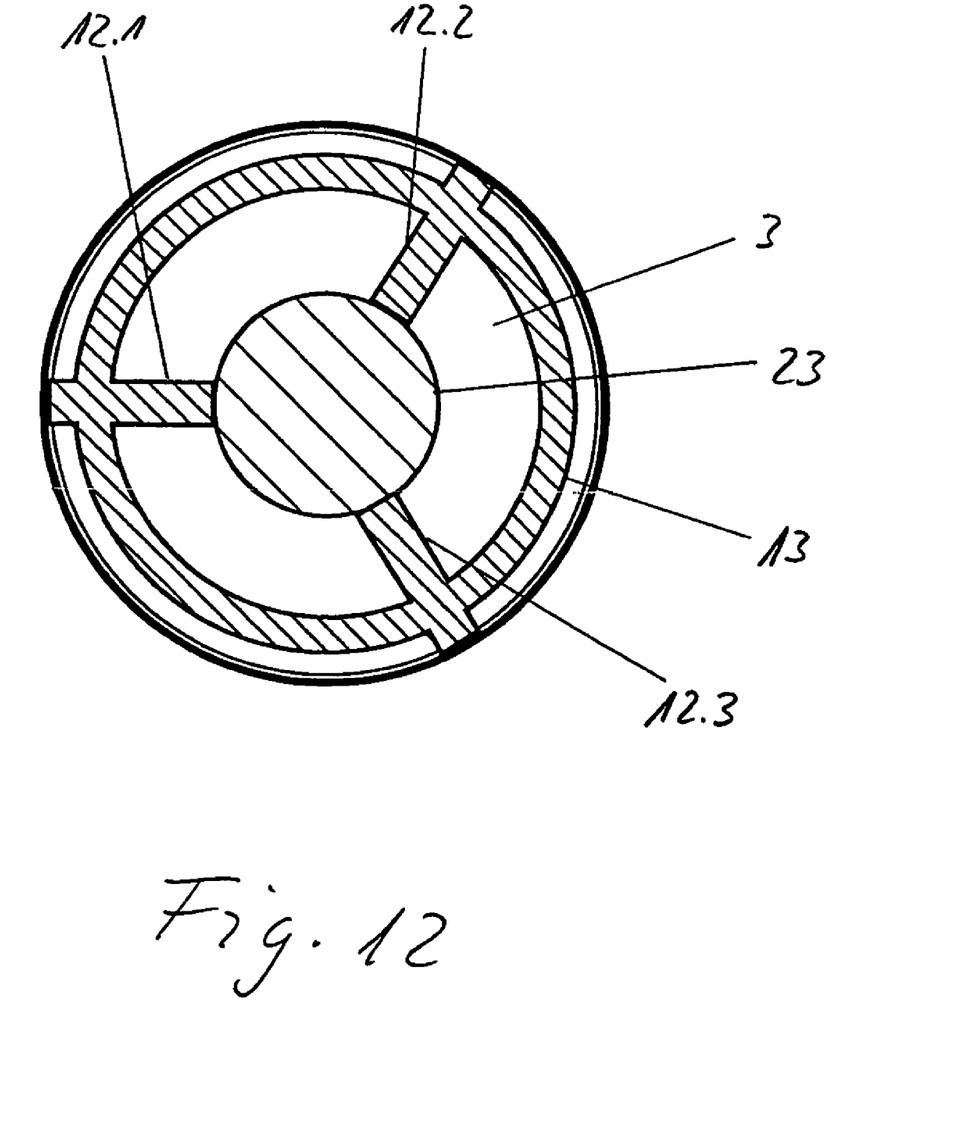
FIG. 12 cross-sections through the outlet region of the axial flow pump in accordance with the embodiment shown in FIG. 11.

FIG. 12 shows a cross-section through the outlet region of the axial flow pump in accordance with the embodiment shown in FIG. 11. In this embodiment, three respective guide vanes 12.1-12.3 are arranged in the outlet region of the axial flow pump and also serve as holding elements for the guide ring 13 and the cap 23. The number of the holding elements or guide vanes can be selected freely in a wide range. Typically, arrangements of two to four guide vanes are provided. Furthermore, the shape and the profile of the holding elements or guide vanes can also be matched to the particular conditions, for example in that axial, obliquely running or curved guide vanes are provided or guide vanes or guide vane edges with a rounded, running out or tapered profile.

Depending on the design, pressure differentials of 150 hPa and more can be generated with the axial flow pump in accordance with the invention. Thanks to the contact-free drive and the contact-free support of the rotor, the axial flow pump can be used as a blood pump. It is advantageous in this connection that the axial flow pump in accordance with the invention has a comparatively low contact area with the main volume flow and that a better washing around of the rotor is possible by the described embodiment of the gap between the housing and the rotor.

The invention claimed is:
1. An axial flow pump, comprising:
a housing having an inlet and an outlet,
an elongate-shaped rotor in the housing, wherein the rotor is provided with a passage in an interior thereof and with at least one spiral-shaped transport element in the passage, wherein the spiral shaped transport element is arranged on the inner surface of the rotor,
wherein
a center of the rotor is open over the entire length of the rotor in an axial direction of the rotor, the transport element extends toward the center of the rotor, the cross section left open within the transport element progressively changes over the length of the rotor, and a pitch of the transport element progressively changes in the axial direction.

2. An axial flow pump in accordance with claim 1, wherein the pitch of the transport element increases toward the outlet.

3. An axial flow pump in accordance with claim 1, wherein at least a part of the rotor contains a permanently magnetic or soft magnetic material, or wherein the rotor includes at least one short-circuit turn.

4. An axial flow pump in accordance with claim 1, further comprising
at least one guide element which is arranged: in an inlet region of the inlet, or between the housing and the rotor, or in an outlet region of the outlet at the housing,
wherein the at least one guide element extends from the housing inwardly and toward a hollow space coaxial with the open center of the rotor.

5. The axial flow pump according to claim 1, further comprising
an electromagnetic drive to drive the rotor, wherein the electromagnetic drive comprises a stator that is provided at the housing, and the rotor or a part thereof is made magnetically active.

6. An axial flow pump in accordance with claim 5, wherein said pump is a blood pump.

7. An axial flow pump in accordance with claim 5, wherein said pump is partly or fully provided with a blood-compatible coating.

8. An axial flow pump in accordance with claim 5, wherein
the stator includes at least one winding configured to generate a rotary magnetic field in operation, and
the electromagnetic drive defines a magnetic bearing for rotatably supporting the rotor.

9. An axial flow pump in accordance with claim 1, wherein the transport element has a rounded or pointed profile.

10. An axial flow pump in accordance with claim 4, wherein the pump comprises at least two respective guide elements arranged in at least one selected from the group consisting of the inlet region and the outlet region at the housing,
wherein the at least two guide elements extend from the housing inwardly and toward the hollow space coaxial with the open center of the rotor.

11. An axial flow pump in accordance with claim 1, wherein an edge of the transport element has a rounded or pointed profile.

* * * * *